(12) United States Patent
Faccioli et al.

(10) Patent No.: US 9,452,001 B2
(45) Date of Patent: Sep. 27, 2016

(54) DISPOSABLE DEVICE FOR TREATMENT OF INFECTIONS OF HUMAN LIMBS

(75) Inventors: Giovanni Faccioli, Monzambano (IT); Soffiatti Renzo, Nogara (IT)

(73) Assignee: TECRES S.P.A., Sommacampagna (Verona) (IT)

( * ) Notice: Subject to any disclaimer, the term of this patent is extended or adjusted under 35 U.S.C. 154(b) by 388 days.

(21) Appl. No.: 13/045,089

(22) Filed: Mar. 10, 2011

(65) Prior Publication Data
US 2011/0208189 A1 Aug. 25, 2011

Related U.S. Application Data

(63) Continuation-in-part of application No. 11/884,663, filed as application No. PCT/IB2006/000317 on Feb. 16, 2006.

(30) Foreign Application Priority Data

Feb. 22, 2005 (IT) ................ VI2005A0049

(51) Int. Cl.
| | |
|---|---|
| *A61B 17/72* | (2006.01) |
| *A61B 17/00* | (2006.01) |
| *A61B 17/56* | (2006.01) |
| *A61M 25/00* | (2006.01) |

(52) U.S. Cl.
CPC ...... *A61B 17/72* (2013.01); *A61B 2017/00004* (2013.01); *A61B 2017/00526* (2013.01); *A61B 2017/561* (2013.01); *A61M 25/007* (2013.01)

(58) Field of Classification Search
CPC A61B 17/846; A61B 17/72; A61B 17/7208; A61B 17/7216; A61B 17/7225; A61B 17/7233; A61B 17/7241; A61B 17/725; A61B 17/7258; A61B 17/7266; A61B 17/7275; A61B 17/7283; A61B 17/7291
USPC ..................................... 606/62–68
See application file for complete search history.

(56) References Cited

U.S. PATENT DOCUMENTS

| | | | | |
|---|---|---|---|---|
| 3,906,550 A | * | 9/1975 | Rostoker ............... | A61B 17/72 29/419.1 |
| 4,038,703 A | * | 8/1977 | Bokros ................... | A61F 2/06 623/2.38 |
| 4,064,567 A | * | 12/1977 | Burstein ............. | A61F 2/30907 623/23.46 |
| 4,065,817 A | * | 1/1978 | Branemark ......... | A61F 2/30907 606/62 |
| 4,158,893 A | * | 6/1979 | Swanson ............... | A61F 2/4241 623/18.11 |
| 4,259,072 A | * | 3/1981 | Hirabayashi ......... | A61C 8/0012 433/173 |
| 4,261,350 A | * | 4/1981 | Branemark ......... | A61F 2/30721 606/62 |
| 4,365,359 A | * | 12/1982 | Raab .................... | A61F 2/30767 427/2.26 |
| 4,492,577 A | * | 1/1985 | Farris ................... | A61C 8/0012 433/173 |
| 4,711,232 A | * | 12/1987 | Fischer ................ | A61B 17/686 411/395 |
| 4,753,657 A | * | 6/1988 | Lee ..................... | A61F 2/30734 623/16.11 |
| 4,790,850 A | * | 12/1988 | Dunn ...................... | A61F 2/08 623/13.19 |

(Continued)

FOREIGN PATENT DOCUMENTS

DE 19605735 6/1977

*Primary Examiner* — Lynnsy Summitt
(74) *Attorney, Agent, or Firm* — Tutunjian & Bitetto, P.C.

(57) ABSTRACT

A disposable device for treatment of infections of human limbs, particularly limbs having long bones susceptible to stabilization by intramedullary nailing. The device includes a tubular member made of a relatively rigid and biologically compatible material, having pores for impregnation with drugs or medicaments for infection treatment prior to or during insertion thereof in the stabilization site. An assembly for treatment of human limb infections including such device.

7 Claims, 11 Drawing Sheets

(56) References Cited

U.S. PATENT DOCUMENTS

| | | | | |
|---|---|---|---|---|
| 4,863,444 A * | 9/1989 | Blomer | A61B 17/60 | 424/423 |
| 4,895,572 A * | 1/1990 | Chernoff | A61F 2/36 | 606/64 |
| 4,913,903 A * | 4/1990 | Sudmann | A61K 9/0024 | 424/422 |
| 4,919,666 A * | 4/1990 | Buchhorn | A61M 31/002 | 606/62 |
| 4,938,772 A * | 7/1990 | Frey | A61F 2/30734 | 623/23.28 |
| 5,018,285 A * | 5/1991 | Zolman | A61F 2/30907 | 29/419.1 |
| 5,030,233 A * | 7/1991 | Ducheyne | A61F 2/30907 | 623/23.54 |
| 5,057,110 A * | 10/1991 | Kranz | A61B 17/72 | 606/62 |
| 5,061,286 A * | 10/1991 | Lyle | A61F 2/30767 | 623/23.63 |
| 5,084,050 A * | 1/1992 | Draenert | A61F 2/30767 | 606/304 |
| 5,098,434 A * | 3/1992 | Serbousek | A61B 17/8625 | 606/308 |
| 5,112,354 A * | 5/1992 | Sires | A61F 2/28 | 600/36 |
| 5,176,712 A * | 1/1993 | Homsy | A61F 2/30767 | 623/23.36 |
| 5,211,664 A * | 5/1993 | Tepic | A61F 2/2846 | 606/60 |
| 5,387,243 A * | 2/1995 | Devanathan | A61F 2/30734 | 128/898 |
| 5,397,359 A * | 3/1995 | Mittelmeier | A61C 8/0012 | 623/1.5 |
| 5,496,375 A * | 3/1996 | Sisk | A61F 2/30907 | 623/23.54 |
| 5,571,193 A * | 11/1996 | Kampner | A61F 2/30734 | 623/23.57 |
| 5,571,204 A * | 11/1996 | Nies | A61F 2/30723 | 623/23.19 |
| 5,618,286 A | 4/1997 | Brinker | | |
| 5,716,358 A * | 2/1998 | Ochoa | A61B 17/68 | 606/301 |
| 5,755,720 A * | 5/1998 | Mikhail | A61F 2/30734 | 606/92 |
| 5,836,949 A * | 11/1998 | Campbell, Jr. | A61B 17/72 | 606/62 |
| 5,919,234 A * | 7/1999 | Lemperle | A61B 17/688 | 128/898 |
| 6,013,104 A * | 1/2000 | Kampner | A61F 2/30734 | 623/22.16 |
| 6,077,076 A * | 6/2000 | Comfort | A61C 8/0009 | 433/173 |
| 6,143,036 A * | 11/2000 | Comfort | A61C 8/0009 | 623/23.49 |
| 6,156,070 A * | 12/2000 | Incavo | A61F 2/30734 | 623/16.11 |
| 6,214,049 B1 * | 4/2001 | Gayer | A61C 8/0006 | 623/16.11 |
| 6,261,289 B1 * | 7/2001 | Levy | A61B 17/7266 | 606/62 |
| 6,319,255 B1 * | 11/2001 | Grundei | A61B 17/70 | 606/246 |
| 6,364,909 B1 * | 4/2002 | McGee | A61L 31/026 | 623/16.11 |
| 6,409,764 B1 * | 6/2002 | White | A61C 8/0006 | 424/424 |
| 6,461,385 B1 * | 10/2002 | Gayer | A61C 8/0006 | 623/23.51 |
| 6,464,728 B1 * | 10/2002 | Murray | A61F 2/30734 | 623/22.42 |
| 6,514,288 B2 * | 2/2003 | Meulink | A61F 2/30767 | 623/23.3 |
| 6,524,344 B2 * | 2/2003 | Yoon | A61F 2/30907 | 623/23.19 |
| 6,596,338 B2 * | 7/2003 | Scott | A61L 27/32 | 427/2.1 |
| 6,679,890 B2 * | 1/2004 | Margulies | A61B 17/742 | 606/60 |
| 6,719,793 B2 * | 4/2004 | McGee | A61L 31/026 | 623/16.11 |
| 6,783,530 B1 * | 8/2004 | Levy | A61B 17/7266 | 606/246 |
| 6,810,880 B1 * | 11/2004 | Jennings, Jr. | A61B 19/08 | 128/849 |
| 6,821,528 B2 * | 11/2004 | Scott | A61L 27/32 | 424/422 |
| 6,863,692 B2 * | 3/2005 | Meulink | A61F 2/3609 | 206/363 |
| 6,974,483 B2 * | 12/2005 | Murray | A61F 2/3609 | 623/22.42 |
| 7,131,995 B2 * | 11/2006 | Biedermann | B21D 41/04 | 623/23.46 |
| 7,192,448 B2 * | 3/2007 | Ferree | A61B 17/164 | 623/18.11 |
| 7,217,283 B2 * | 5/2007 | Pedrozo | A61B 17/742 | 623/1.13 |
| 7,534,451 B2 * | 5/2009 | Erbe | A61B 17/80 | 424/422 |
| 7,641,688 B2 * | 1/2010 | Lesh | A61F 2/0059 | 606/192 |
| 7,659,219 B2 * | 2/2010 | Biran | A61L 31/146 | 424/422 |
| 7,723,395 B2 * | 5/2010 | Ringeisen | A61B 17/0642 | 521/50 |
| 7,892,290 B2 * | 2/2011 | Bergin | A61F 2/30734 | 623/23.22 |
| 7,909,864 B2 * | 3/2011 | Sheu | A61F 2/30734 | 623/23.22 |
| 7,909,883 B2 * | 3/2011 | Sidebotham | A61F 2/2814 | 623/11.11 |
| 7,947,042 B2 * | 5/2011 | Osman | A61B 17/72 | 606/62 |
| 8,007,498 B2 * | 8/2011 | Mische | A61B 17/7258 | 606/100 |
| 8,021,432 B2 * | 9/2011 | Meridew | A61F 2/30721 | 623/22.32 |
| 8,075,312 B2 * | 12/2011 | Collins | A61C 8/0006 | 433/173 |
| 8,128,626 B2 * | 3/2012 | Justin | A61B 17/7044 | 606/62 |
| 8,147,492 B2 * | 4/2012 | Justin | A61B 17/7044 | 606/63 |
| 8,157,722 B2 * | 4/2012 | Arnal | A61B 17/06066 | 600/30 |
| 8,162,943 B2 * | 4/2012 | Justin | A61B 17/7044 | 606/63 |
| 8,167,881 B2 * | 5/2012 | Justin | A61B 17/7044 | 606/63 |
| 8,221,504 B2 * | 7/2012 | Richelsoph | A61L 27/306 | 424/422 |
| 8,226,659 B2 * | 7/2012 | Rabiner | A61B 17/7097 | 606/63 |
| 8,241,655 B2 * | 8/2012 | Chudzik | A61L 27/34 | 424/133.1 |
| 8,257,624 B2 * | 9/2012 | Favis | A61L 27/18 | 264/288.8 |
| 8,287,538 B2 * | 10/2012 | Brenzel | A61B 17/7225 | 606/62 |
| 8,287,915 B2 * | 10/2012 | Clineff | A61B 17/80 | 424/602 |
| 8,292,967 B2 * | 10/2012 | Brown | A61B 17/0401 | 623/23.19 |
| 2002/0147451 A1 * | 10/2002 | McGee | A61L 31/026 | 606/62 |
| 2003/0065397 A1 * | 4/2003 | Hanssen | A61F 2/30734 | 623/20.32 |
| 2003/0082233 A1 * | 5/2003 | Lyons | C07K 14/51 | 424/484 |
| 2004/0172026 A1 * | 9/2004 | Ekholm | A61B 17/72 | 606/62 |
| 2004/0193270 A1 * | 9/2004 | DiMauro | A61L 27/3834 | 623/17.11 |
| 2005/0015154 A1 * | 1/2005 | Lindsey | A61B 17/68 | 623/23.46 |

(56) References Cited

U.S. PATENT DOCUMENTS

| | | | | |
|---|---|---|---|---|
| 2005/0043585 A1* | 2/2005 | Datta | A61F 2/0077 | 600/153 |
| 2005/0043797 A1* | 2/2005 | Lee | A61B 17/686 | 623/17.11 |
| 2005/0079199 A1* | 4/2005 | Heruth | A61M 27/006 | 424/423 |
| 2005/0153156 A1* | 7/2005 | Miyoshi | B22D 19/14 | 428/613 |
| 2005/0175657 A1* | 8/2005 | Hunter | A61B 17/11 | 424/422 |
| 2005/0191248 A1* | 9/2005 | Hunter | A61B 17/11 | 424/50 |
| 2006/0025848 A1* | 2/2006 | Weber | A61F 2/82 | 623/1.15 |
| 2006/0051393 A1* | 3/2006 | Heruth | A61L 27/54 | 424/423 |
| 2006/0105012 A1* | 5/2006 | Chinn | A61L 27/34 | 424/422 |
| 2006/0149362 A1* | 7/2006 | Pedrozo | A61B 17/742 | 623/1.35 |
| 2006/0241776 A1* | 10/2006 | Brown | A61B 17/0401 | 623/20.16 |
| 2007/0083202 A1* | 4/2007 | Eli Running | A61B 17/72 | 606/62 |
| 2007/0088443 A1* | 4/2007 | Hanssen | A61F 2/30734 | 623/23.46 |
| 2007/0112432 A1* | 5/2007 | Reiley | A61B 17/15 | 623/21.18 |
| 2007/0116734 A1* | 5/2007 | Akash | A61F 2/30 | 424/423 |
| 2007/0190108 A1* | 8/2007 | Datta | A61L 27/48 | 424/423 |
| 2007/0244485 A1* | 10/2007 | Greenhalgh | A61F 2/4455 | 606/86 R |
| 2008/0039845 A1* | 2/2008 | Bonutti | A61B 17/0401 | 606/62 |
| 2008/0154378 A1* | 6/2008 | Pelo | A61B 17/866 | 623/17.16 |
| 2008/0255560 A1* | 10/2008 | Myers | A61B 17/7225 | 606/63 |
| 2008/0281430 A1* | 11/2008 | Kelman | A61F 2/30734 | 623/23.23 |
| 2009/0024204 A1* | 1/2009 | Greenhalgh | A61B 17/7098 | 623/1.15 |
| 2009/0076508 A1* | 3/2009 | Weinans | A61F 2/30771 | 606/62 |
| 2009/0143781 A1* | 6/2009 | Mische | A61B 17/7225 | 606/63 |
| 2009/0317762 A1* | 12/2009 | Schiefer | A61C 8/0012 | 433/173 |
| 2010/0042214 A1* | 2/2010 | Nebosky | A61B 17/56 | 623/16.11 |
| 2010/0055149 A1* | 3/2010 | Li | A61F 2/04 | 424/425 |
| 2010/0087821 A1* | 4/2010 | Trip | A61B 17/7208 | 606/63 |
| 2010/0145452 A1* | 6/2010 | Blaylock | A61F 2/30 | 623/16.11 |
| 2010/0226960 A1* | 9/2010 | Chudzik | A61K 9/0024 | 424/426 |
| 2010/0262144 A1* | 10/2010 | Kelman | A61F 2/34 | 606/62 |
| 2010/0305712 A1* | 12/2010 | Ringeisen | A61B 17/0642 | 623/23.5 |
| 2011/0014289 A1* | 1/2011 | Datta | A61L 27/18 | 424/486 |
| 2011/0257623 A1* | 10/2011 | Marshall | A61L 27/56 | 604/500 |
| 2011/0307073 A1* | 12/2011 | Teoh | A61F 2/28 | 623/23.61 |

* cited by examiner

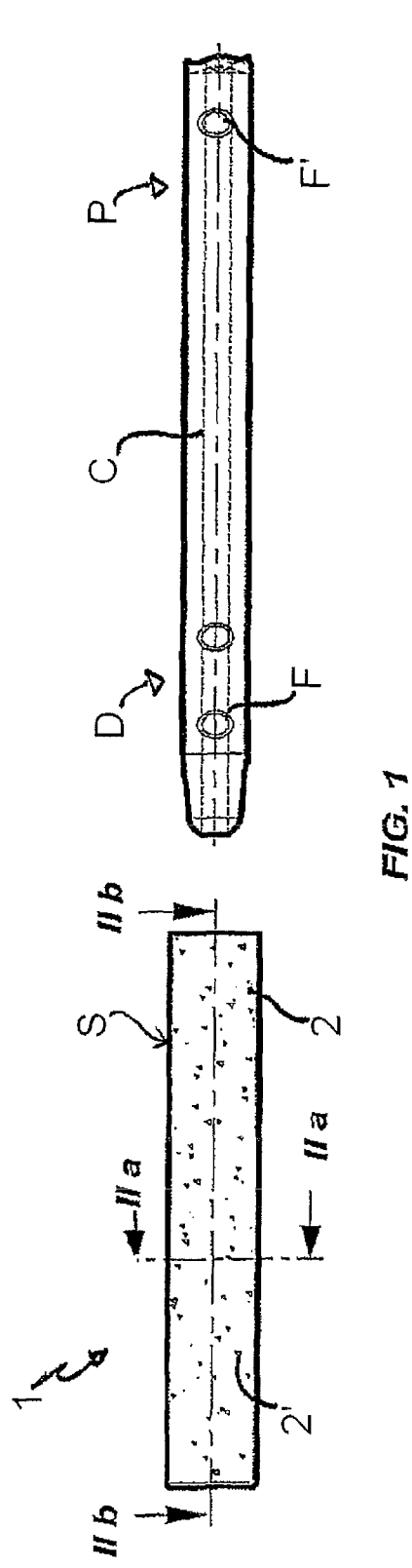
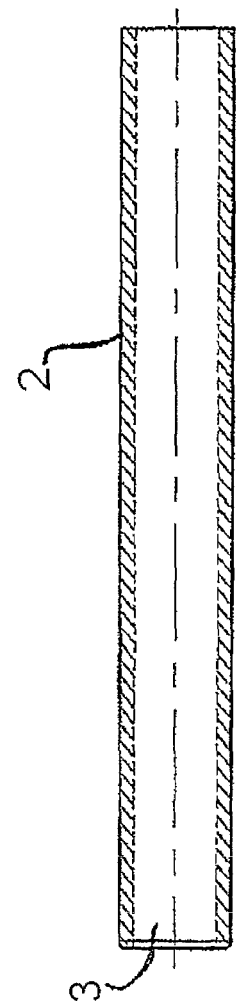
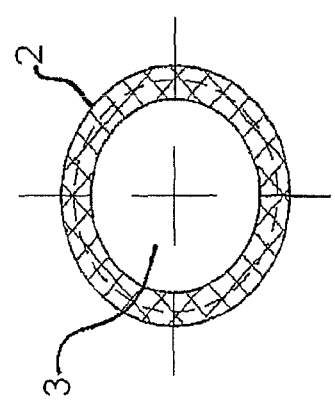
FIG. 1
FIG. 2a
FIG. 2b

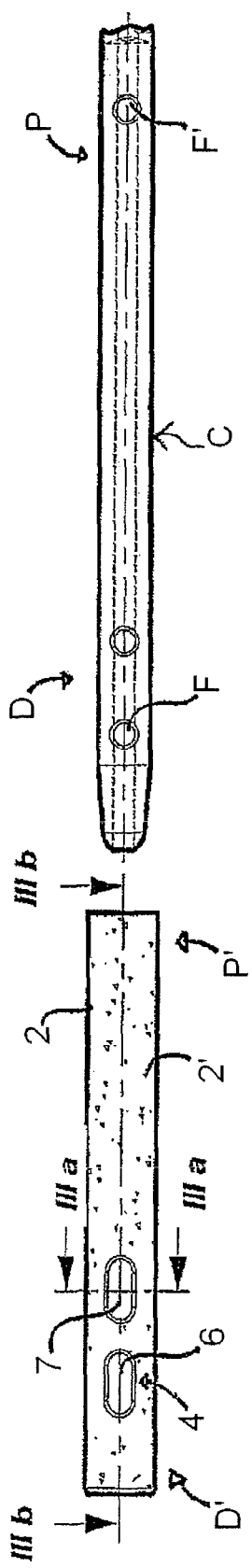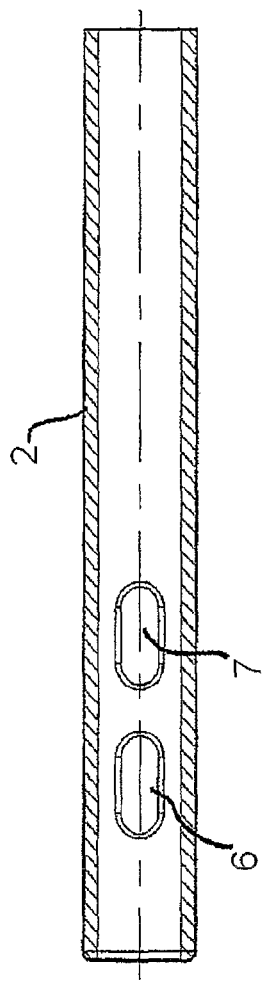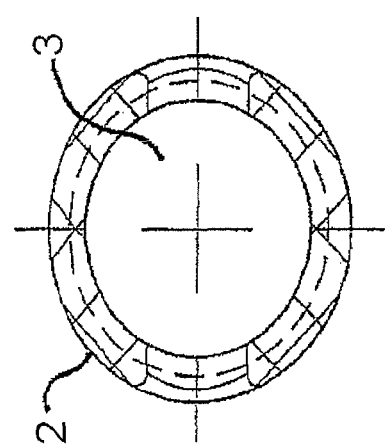
FIG. 3
FIG. 3b
FIG. 3a

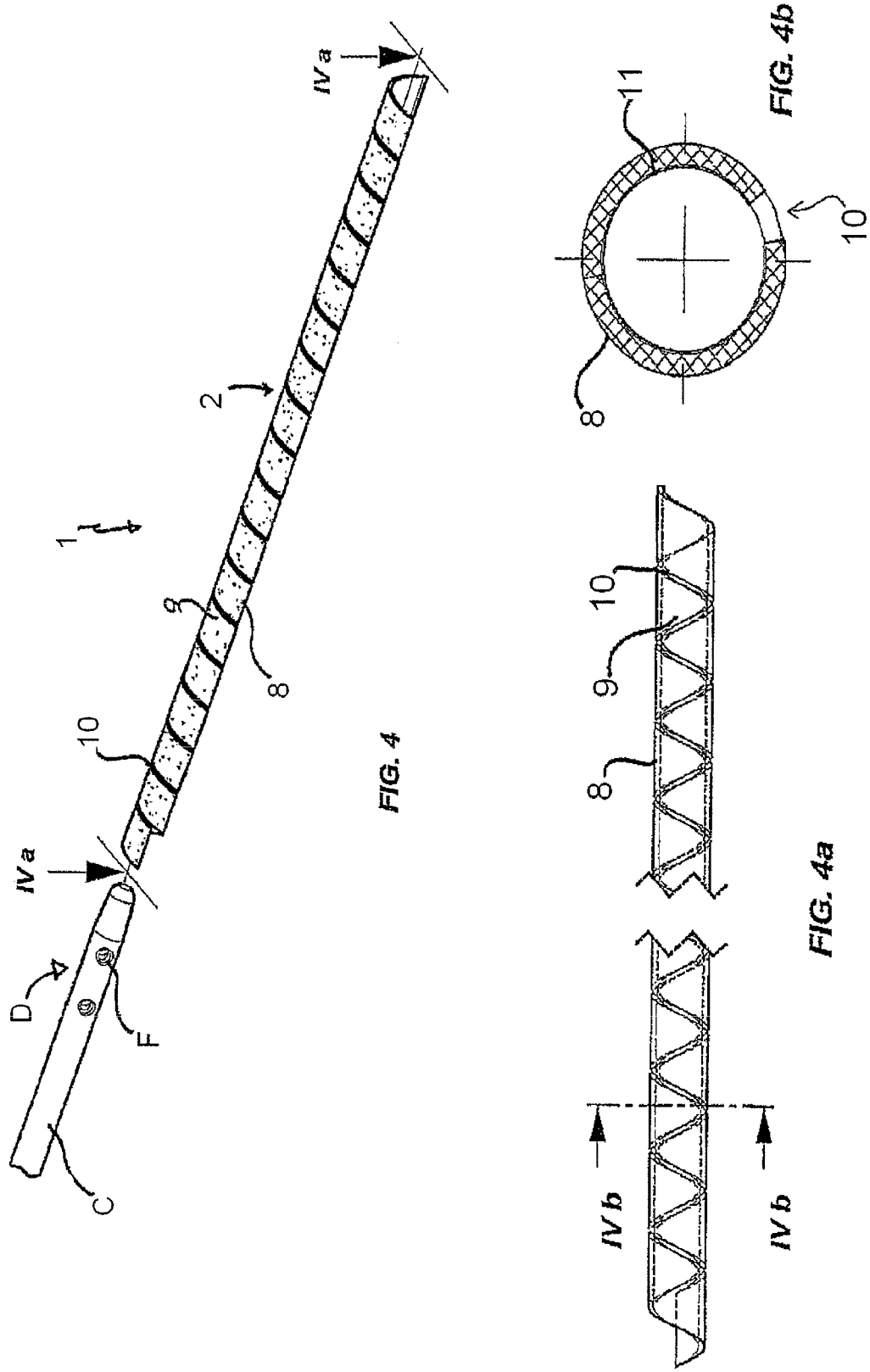

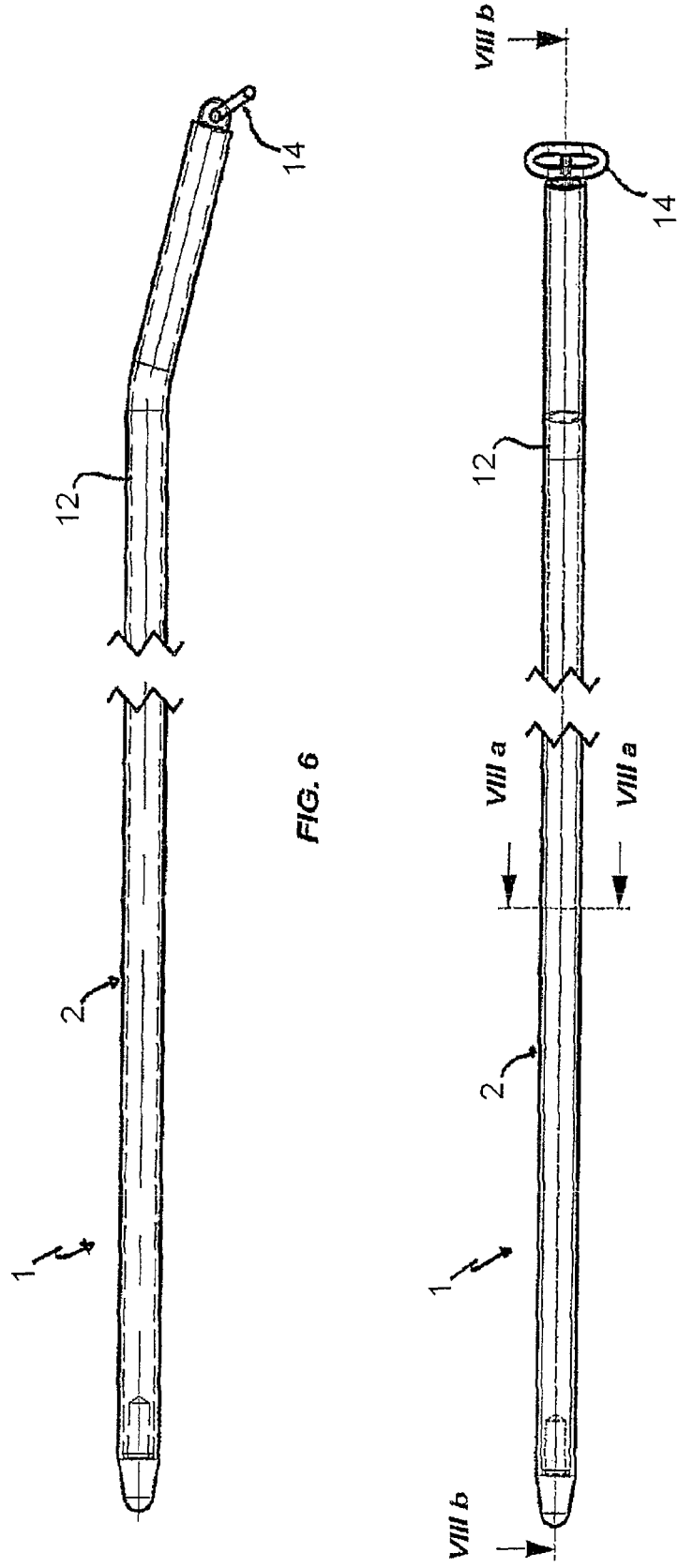

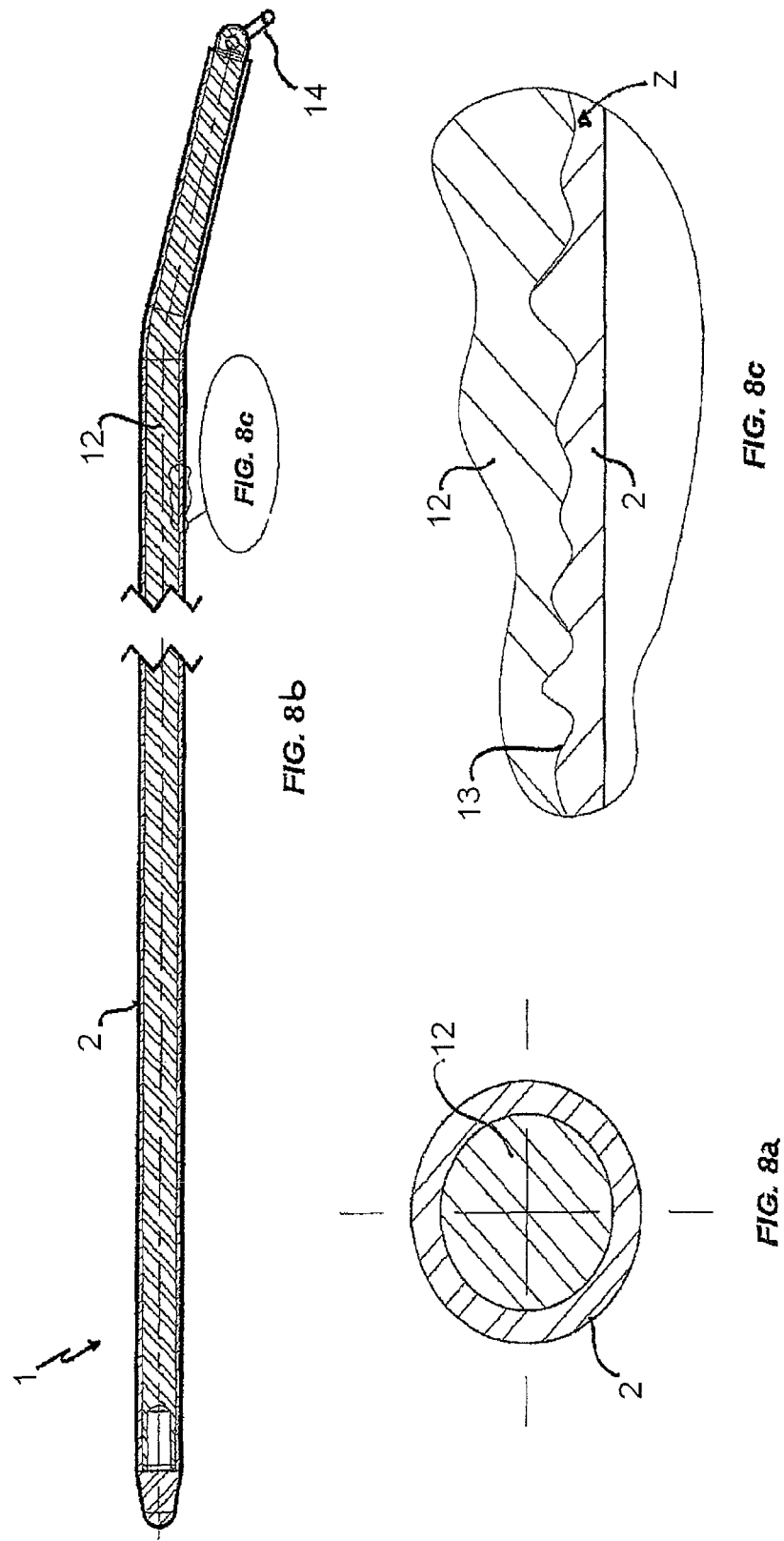

DISPOSABLE DEVICE FOR TREATMENT OF INFECTIONS OF HUMAN LIMBS

CROSS-REFERENCE TO RELATED APPLICATIONS

This is a continuation-in-part of application Ser. No. 11/884,663 filed Aug. 20, 2007 and which is currently pending, the disclosure of which is incorporated herein by reference.

FIELD OF THE INVENTION

The present invention is applicable in the technical field of surgical instruments, and particularly relates to a disposable device for treatment of infections of human limbs, more specifically limbs having long bones susceptible to stabilization by intramedullary nails.

BACKGROUND OF THE INVENTION

Stabilization of long bones of the human body, following fractures, malformations or similar pathologic situations is known to be attained by using well-known devices such as intramedullary nails, consisting of more or less curved hollow or solid metal rods, which are fitted into the intramedullary cavity of the bones to be stabilized and are anchored to the stumps or parts to be stabilized by transverse-pins or screws, typically in the distal and proximal region of the limb. Once the fracture has been stabilized and fixed, the pins are removed and the nail is extracted from the medullary canal.

One problem associated to such treatment, in addition to the invasiveness of the implantation procedure, is the establishment of infection foci, which may locally develop due to the incompatibility of metal with the spongy medullary tissue and due to the bacteria that normally come in contact with the implantation site.

In order to minimize such drawbacks, it is highly recommended that the implantation of the above devices occurs in wholly sterile conditions, and that the relevant part is treated with substances adapted to prevent and/or treat such infections.

In an attempt to at least partly obviate the above drawbacks, solutions have been developed to allow in situ application of the above substances, alone or added to bone cement.

The U.S. Pat. No. 4,863,444 discloses a carrier shaped like a stick through which an antibiotic could be distributed. The stick, due to its elongated configuration, can be inserted into the channel provided through the skin and the soft tissues for the accommodation of an external fixture comprising a screw or a nail introduced into the bone.

A solution is known in which a cover for the stabilizer device is made by using molds at the factory or directly at the surgical site immediately before implantation of such device.

This solution also has several apparent drawbacks.

First, it is a substantially manual solution, which requires special skills from the operator, who has to be properly trained therefor. Such an operation further involves many processing scraps, thereby causing a high material waste and an increase of the overall processing costs.

The thus covered device is also exposed for a sufficiently long time to air and to contact with foreign material, which involves a high risk of attack by bacteria and contaminants.

Furthermore, the covered device which comes out of the mold will exhibit many burrs along its longitudinal extension, which will have to be removed for proper positioning, thereby involving longer implantation times and consequent discomfort for the patient.

A further aspect of the invention relates to the need of temporarily replacing an intramedullary nail for one of several different reasons, such as recidivation or dislocation of the implant, normally followed by surgical site infections.

In these situations, the existing intramedullary nail has to be removed and the implant site has to be treated before insertion of the new nail. In the meantime, the geometry of the site shall be maintained unchanged, to prevent shortening and deformation of tissues, by providing a spacer device which can also prevent and/or treat the infections due to the old and new implant.

SUMMARY OF THE INVENTION

It is a main object of the present invention to overcome the above mentioned drawbacks by providing a device for infection treatment that exhibits high efficiency and cost effectiveness. A particular object is to provide a ready-to-use device for treatment of infections, which avoids the use of skilled personnel.

A further object is to provide a device for treatment of infections that allows to reduce the time of exposure thereof to the environment and assures highly sterile conditions.

Another object is to provide a device for treatment of infections that allows an optimized use of materials.

Yet another object is to provide a device for treatment of infections that allows fast removal of the cover.

These objects, as well as other objects that will be more apparent hereafter, are fulfilled by a disposable device according to an aspect of the present invention.

This particular arrangement of the invention provides a ready-to-use device for treatment of infections, while avoiding the need of skilled personnel to fabricate it.

Furthermore, this particular arrangement of the invention allows an optimized use of materials, and wholly eliminates processing scraps, while reducing the time required for fitting such cover onto the nail.

Preferably, the device for treatment of infections may be made of a material selected from the group including bone cements and reabsorbable or biodegradable bone cements. Thus, the device will be biologically compatible with the limb to be treated.

This tubular member may be suitably hollow, to allow fitting thereof onto an intramedullary nail.

Thanks to this feature, the device of the invention allows an optimized use of the base material, and increases cost-effectiveness.

In accordance with a further aspect of the invention, there is provided an assembly for treatment of infections of human limbs according which comprises a sterile enclosure or blister, which is designed to contain a tubular member as described above.

This particular arrangement of the invention provides a device for treatment of infections which assures high sterility.

According to one aspect, a disposable device for treatment of infections of human limbs is provided comprising an intramedullary nail suitable for stabilization of human limbs with a distal region and a proximal region, and a tubular member comprised of a relatively rigid and biologically compatible material and configured to at least partially cover said intramedullary nail, said material comprising at least one of a porous or spongy material, said tubular member having a proximal region and a distal region and pores integrated arbitrarily throughout the material of said tubular member, said material of the tubular member being impregnated with drugs or medicaments for treatment of infections, prior to or during insertion thereof in the stabilization site.

According to another aspect, a disposable device for treatment of infections of human limbs is provided comprising a tubular member made of a relatively rigid and biologically compatible material, said material comprising at least one of a porous or spongy material, said tubular member having pores integrated arbitrarily throughout the material of said tubular member, wherein the material of said tubular member is configured to be impregnated with drugs or medicaments for treatment of infections, prior to or during insertion thereof in the stabilization site, said pores being disposed in a casual pattern and located in the outer surface and/or in the inner part of said tubular member, wherein said tubular member is internally associated with a stable reinforcement core made of a relatively rigid metal or non-metal material, whereby said device forms an intramedullary nail suitable for stabilization of said human limbs.

According to yet another aspect, a device providing an intramedullary nail for treatment of infections of human limbs is provided comprising a stable reinforcement core made of a relatively rigid metal or non-metal material, said stable reinforcement core having an external surface, and a tubular member made of a biologically compatible material, said material comprising at least one of a porous or spongy material, said tubular member being intimately adherent to the external surface of said stable reinforcement core, said material of the tubular member including pores configured to be impregnated with drugs or medicaments for treatment of infections, prior to or during insertion thereof in the stabilization site; and said pores being integrated arbitrarily throughout the material of said tubular member and disposed in a casual pattern and located in the outer surface and/or in the inner part of said tubular member.

According to yet another aspect, a method for providing a device for treatment of infections of human limbs is provided comprising the steps of providing a solution comprised of a base material composed of a polymer or bone-cement material with an organic or aqueous solvent in which the concentration of the base material versus the solvent is about 1% (w/w) to about 75% (w/w), adding a drug or other medicament in the solution at a concentration versus the polymer of about 5% (w/w) to about 65% (w/w), homogenizing the solution, applying the solution to an intramedullary nail through immersion of the intramedullary nail in the solution and emersion of the intramedullary nail, waiting about 10-60 minutes, and repeating the steps of applying and waiting alternatively at least other two times.

Further features and advantages of the invention will be more apparent from the detailed description of a preferred, non-exclusive embodiment of a disposable device according to the invention, which is described by way of non-limiting example with the help of the annexed drawings.

BRIEF DESCRIPTION OF THE DRAWINGS

FIG. 1 is a side view of one embodiment of the device according to the invention;
FIG. 2a is a sectioned view of the device as shown in FIG. 1, taken along a plane IIa-IIa
FIG. 2b is a sectioned view of the device as shown in FIG. 1, taken along a plane IIb-IIb;
FIG. 3 is a side view of a further embodiment of the device according to the invention;
FIG. 3a is a sectioned view of the device as shown in FIG. 3, taken along a plane IIIa-IIIa;
FIG. 3b is a sectioned view of the device as shown in FIG. 3, taken along a plane IIIb-IIIb;
FIG. 4 is an axonometric view of another configuration of the device according to the invention;
FIG. 4a is a sectioned view of the device as shown in FIG. 4, taken along a plane IVa-IVa;
FIG. 4b is a sectioned view of the device as shown in FIG. 4, taken along a plane IVb-IVb;
FIG. 6 is a side view of another configuration of the device according to the invention;
FIG. 7 is a further side view of the device as shown in FIG. 6;
FIG. 8a is a sectioned view of the device as shown in FIG. 7, taken along a plane VIIIa-VIIIa;
FIG. 8b is a sectioned view of the device as shown in FIG. 7, taken along a plane VIIIb-VIIIb;
FIG. 8c is an enlarged view of a detail of FIG. 8b.

DETAILED DESCRIPTION OF PREFERRED EMBODIMENTS

Figure 5:
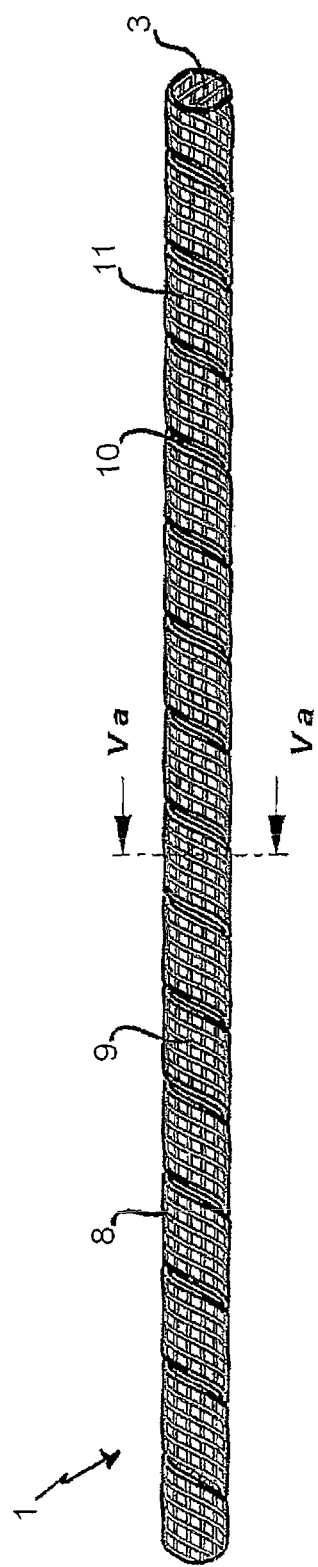
FIG. 5 is a side view of a further embodiment of the device of FIG. 4.
Figure 5A:
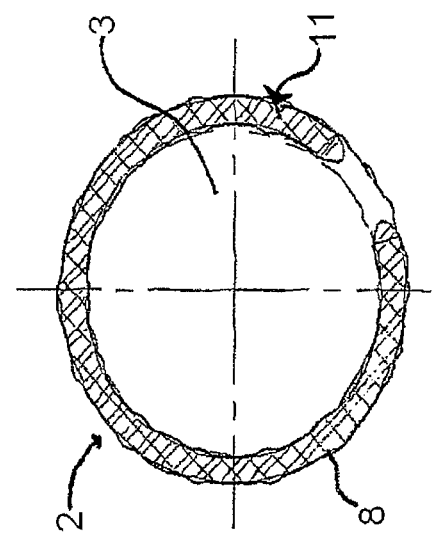
FIG. 5a is a sectioned view of the device as shown in FIG. 5, taken along a plane Va-Va.

Referring to the above figures, a device of the invention, generally denoted by numeral 1, is of the disposable type and will be particularly designed for stabilization of limbs having long bones by intramedullary nailing. Intramedullary nails or rods are used to align and stabilize fractures and are inserted longitudinally into the medullary canal in the center of the long bones of the extremities (e.g. femur or tibia).

The device includes a tubular member 2 made of a biologically compatible material, which may also be of the reabsorbable or biodegradable type.

The device includes a tubular member 2 is made of a biologically compatible material, preferably selected from bone cements.

In a version of the invention, the compatible material of which the tubular member 2 is made is rigid.

The material of which is made the tubular member 2 may be insoluble, and therefore permanent, or soluble, and therefore may be reabsorbed in the human body.

The insoluble material may be obtained by a dispersion of polymers of polymethylmethacrylate (PMMA) and/or PMMA esters, such as butylmethacrylate, etcetera, and/or co-polymers, such as the PMMA-Polymethylstyrene, etcetera, in an organic solvent as, for example, methylmethacrylate monomer, MMA, chloroform, or other organic solvent being suitable to melt the PMMA and/or the PMMA esters and/or co-polymers, in which possible drugs or other medicaments may be added. The solvent may be also water.

The soluble material, instead, may be obtained by a dispersion of polymers soluble in the human body, such as polyglycolic acid (PGA), polylactic acid (PLA), copolymers of polyglycolic acid and polylactic acid (PGA-PLA), copolymers of L polylactic acid and polyglycolic acid (PLLA co PGA), copolymers of L-D-polylactic acid and trimethylene carbonate (PLDA co TMC), polyvinylpyrrolidone (PVP) derivates, polyvinylchloride (PVC), amide or cellulose derivates, etc. and an organic solvent, such as methylmethacrylate, chloroform, or other organic solvent being suitable to melt the above-mentioned polymers, in which possible drugs or other medicaments may be added. The solvent may be also water.

The insoluble and soluble materials are applicable on an intramedullary nail C, after their dispersion or solubilisation in suitable organic, inorganic and/or aqueous solvents.

The above mentioned materials may comprise all optically active isomers or racemic forms.

According to one embodiment, the tubular member 2 may be comprised of a material comprising at least a porous or spongy material.

According to an aspect of the present invention, the tubular member 2 has pores 2' configured to be impregnated with drugs or medicaments for treatment of infections, such as antibiotics, growth promoters, anti-inflammatory and/or antitumor drugs.

In the present specification, the term "pores" means: a small space or a distance from the molecules that compose a body, specifically, the tubular member 2.

In accordance with a first version of the invention, the tubular member 2 has a central axial cavity 3 for the passage of an intramedullary nail C that is at least partially covered by the tubular member 2 itself.

In this first version, the tubular member 2 is obtained by the reaction of the above-mentioned substances and, when inserted in the stabilization site, the reaction has already been concluded: the material is already polymerized and it is porous and therefore used for drugs or other medicaments release.

The pores 2' have a micrometrical dimension and are advantageously naturally obtained by the polymerization reaction. This polymerization reaction starts at room pressure and the air and vapors of the monomer or of the other type of organic solvent, searching for an escape way, create the porosity.

When the solvent evaporates, it creates in the material of the tubular member 2 some escape paths that are the pores 2' from which, in a second moment, the drugs or medicaments are released.

Due to the fact that the impregnation of the tubular member 2 is enabled by way of pores 2' distributed on the tubular member 2 itself, the time of impregnation may be controlled. For example, impregnation may occur at various desired times, such as prior to or during insertion into a stabilization site, or even prior to packaging of the device 1.

The pores 2' are present on the external surface S and into the tubular member 2. The pores 2' may be interconnected and are disposed in a casual pattern of distribution. The pores 2' are natural and of a micrometrical size. Preferably, the pores 2' are not through-pores, i.e., they do not form a direct, unimpeded path between the outer and inner surfaces of the tubular member 2.

In a version of the invention, the pores 2' have a size of about 100-200 micrometers. In this case, the pores 2' are large and may be produced, for example, by the presence of water dispersed in the material of the tubular member 2, i.e. the cement mass. The water is insoluble in the fluid cement mass and therefore it generates a phase separation. During the cement polymerization, the phase separation generates a solid cement matrix in which the pores 2' or micro-channels are displaced.

In a version of the invention, the pores 2' may have a dimension of about 1-100 micrometers in order to avoid the bone tissue growth through them, and preferably of about 100 micron.

The pores 2', and/or the tubular member 2 through the pores 2', may be impregnated with drugs or medicaments for treatment of infections. The pores 2', which are not necessarily through-pores, enable the retention of the drugs or medicaments within the structure of the tubular member 2, and the release of these substances in the external environment, for example the bone. The pores 2' are not in direct communication with the central cavity 3 or with the internal nail or core of the device 1. In fact the pores 2' are blocked or sealed by the nail or the core inserted into the tubular member. For example, the pores 2' act like little tanks, to retain the above-indicated drugs or medicaments, which they release during the time when they are in contact with the implantation site to be treated.

In one version, the drugs or medicament may be in a dry form in order to be mixed with the material of which the tubular member 2 is made. In this way, these substances are directly contained in the tubular member 2 and the pores 2' provide a path for the release of these substances from the inside the tubular member 2 itself to the outside.

Alternatively, the tubular member 2 may not directly contain the above-indicated drugs and medicaments but, being porous or spongy thanks to the pores 2', it is suitable for being soaked in these substances that are in a fluid form at the moment of the implantation of the device 1 in the patient.

In a version of the invention, the tubular member 2 may be quickly removed from the nail C, thereby allowing simple replacement of the latter after proper sterilization.

Furthermore, the tubular member 2 may comprise connection means 4 for anchorage thereof to the nail C, which connections means preferably comprise an adhesive material 5 interacting with the member 2 and the intramedullary nail C on which it is fitted. Conveniently, the material 5 may be uncured bone cement, designed to partly cover both the tubular member 2 and the intramedullary nail C on which it is fitted and preferably laid or injected in at least one through cavity 6 of the tubular member 2.

Figure 11:
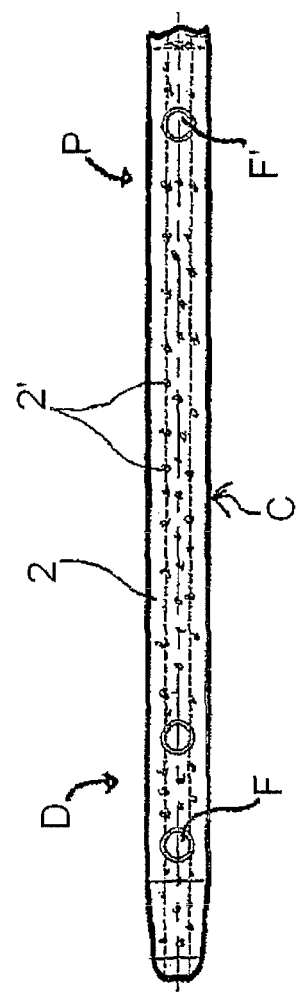
FIG. 11 is a side view of a further embodiment of the device of FIG. 1.

In accordance with another version of the invention, as showed in FIG. 11, the tubular member 2 may be obtained by applying, on the intramedullary nail C, a solution formed by a combination of bone-cement and/or other polymer material and chloroform or one of the above-mentioned organic solvents or water. When the chloroform or the organic solvent or water evaporates, a thin layer of porous bone-cement or polymer material remains on the intramedullary nail C. The evaporation and/or the polymerization of chloroform or the organic solvent or water determines the deposition of a solidified layer of bone-cement or polymer material, that constitutes the tubular member 2, and at the same time the formation, as explained above, of pores 2' that can be at most interconnected and distributed in a casual and arbitrary manner. The pores 2' may have a size of about 100-200 micrometers.

The tubular member 2 has a thickness which dimension depends on the number of applications of the above-indicated solution. The thickness of the tubular member 2 may vary from about 10 micrometers to 1000 micrometers.

When the thickness of the tubular member 2 is about 10 micrometers, it realise a sort of barrier against the bone tissue growth. This is particularly useful for Titanium nails—more than for hard steel AISI 316L or Cobalt-Chrome alloys nails—because the tubular member 2 creates a barrier against the close encapsulation of the bone tissue on the nail which makes difficult the removal of the nail itself.

The thickness of the tubular member of about 100-400 micrometers is useful for drugs or other medicaments delivery; if the thickness increases over 600 micrometers, the drug delivery period will be longer as there is a bigger quantity of drug or other medicaments incorporated in the tubular member 2.

However, if the tubular member has a thickness greater than 250 micron, the size of the intramedullary nail varies: therefore, in a version of the invention it is avoided.

As above explained, the pores 2' may be impregnated with drugs or medicaments for treatment of infections: the drugs or medicament may be in a dry form in order to be mixed with the material of which is made the tubular member 2. In this way, these substances are directly contained in the tubular member 2 and the pores 2' provide a path for the release of these substances from the inside the tubular member 2 itself.

Alternatively the tubular member 2 does not contain directly the above-indicated drugs and medicaments but, being porous or spongy thanks to the pores 2', is suitable for being soaked by these substances that are in a fluid form at the moment of the implantation of the device 1 in the patient.

In a version of the present invention, the tubular member 2 comprises a wall, of the above-indicated materials, applied by at least one immersion of the intramedullary nail C in the above-solutions. In other versions, the above-solution can be painted, and/or sprayed, and/or impregnated, and/or embedded, onto the intramedullary nail C, thus creating the wall comprised in the tubular member 2. The wall could have various thicknesses depending on the thickness of the applied material, the number of applications and the time of application.

The pores 2' of the present invention, obtained as explained above, are disposed and integrated in a very casual and arbitrary pattern and manner throughout the tubular member 2, e.g., on the outer and inner surfaces as well as internally throughout and within the tubular member 2.

The pores 2', thanks to the fact that are formed naturally during the tubular member 2 formation, do not require a specific realizing or creation step and therefore makes the production of the device 1 easier, quicker and cheaper, unlike known devices that comprise tubular members in which holes or ducts have to be predisposed and operatively created or obtained in the device itself.

In accordance with a version of the invention, the tubular member 2 may be substantially continuous and have a predetermined length, preferably corresponding at least to the distance between the holes F and F' in the distal and proximal regions D, P respectively of the intramedullary nail C, as shown in FIG. 1. Thanks to this feature of the invention, the tubular member 2 may be coupled to the intramedullary nail C in a still more stable and less invasive manner.

Advantageously, as particularly shown in FIG. 3, in addition to the cavity 6, a hole 7 may be provided in the proximal region P' or distal region D' of the member 2 for the passage of corresponding screws for anchorage of the intramedullary nail C, not shown in the figures. The screws will firmly secure the nail C, with the device 1 thereon, to the bone to be stabilized, to increase the stability of the treatment. This way of securing of the nail C, and of the tubular member 2, to the bone to be stabilized, prevent the utilization of bone-cement that, when finally cured, raises high reaction temperatures and produces monomers that have the disadvantageous biological effect on the bone, killing the bone tissue.

According to a version of the invention, showed in FIGS. 4 and 5, the tubular member 2 may be a strip 8 of base material, which is wound in a substantially helical shape. Suitably, the turns 9 of such helical shape may be equally spaced, to define a through cavity 10, also having a substantially helical shape.

Preferably, the strip 8 may include an inner and/or outer reinforcement layer 11, made from a woven or non woven fibrous material, preferably of the mesh type.

According to a version of the invention, showed in FIGS. 6-8, the tubular member 2 may be provided with a stable reinforcement core 12, which is made of a relatively rigid metal or non-metal material, to actually define, as a whole, a spacer assembly.

Advantageously, the core 12 may have an irregular outer surface 13, defining an externally threaded anchorage area Z for the member 2.

According to another embodiment, the above-mentioned solution for obtaining a tubular member 2 may be painted onto the core 12, and may be joined to the core 12 due to adhesion (e.g., due to mechanical and/or chemical-physical properties). For example, the mechanical adhesion may be due to irregularity of the core's surface, such as microcavities or undercuts 13, into which the tubular member's material enters. An example of the chemical-physical adhesion may be due to the attraction induced by molecular weak forces, for example Van der Waals forces, exerted between the different materials (e.g., of the tubular member 2 and of the reinforcement core 12).

Furthermore, a gripping member 14, preferably a ring, may be provided at the proximal end of the reinforcement core 12, to facilitate removal of the spacer assembly.

Here again the tubular member 2 may be impregnated with drugs or medicaments for treatment of infections, such as antibiotics, growth promoters, anti-inflammatory and/or antitumor drugs. Impregnation may occur prior to packaging of the device or up on insertion thereof on-site by the surgeon, as explained above.

Figure 9:
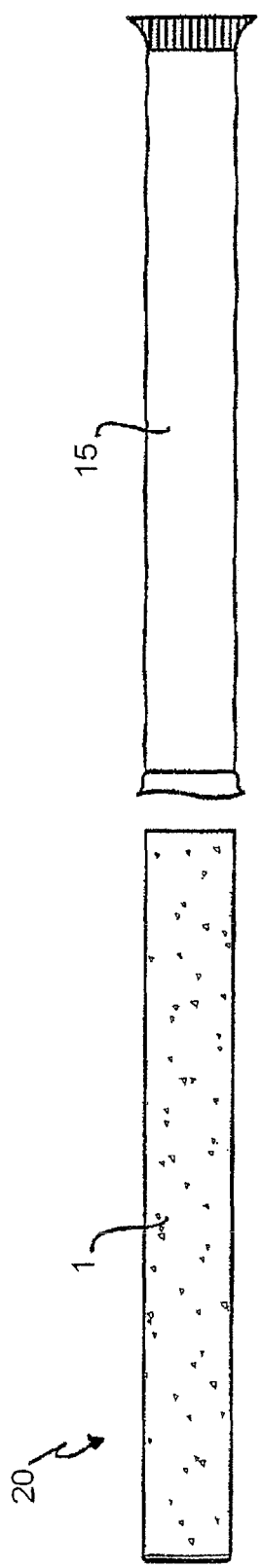
FIG. 9 is a side view of the assembly according to the invention.
Figure 10:
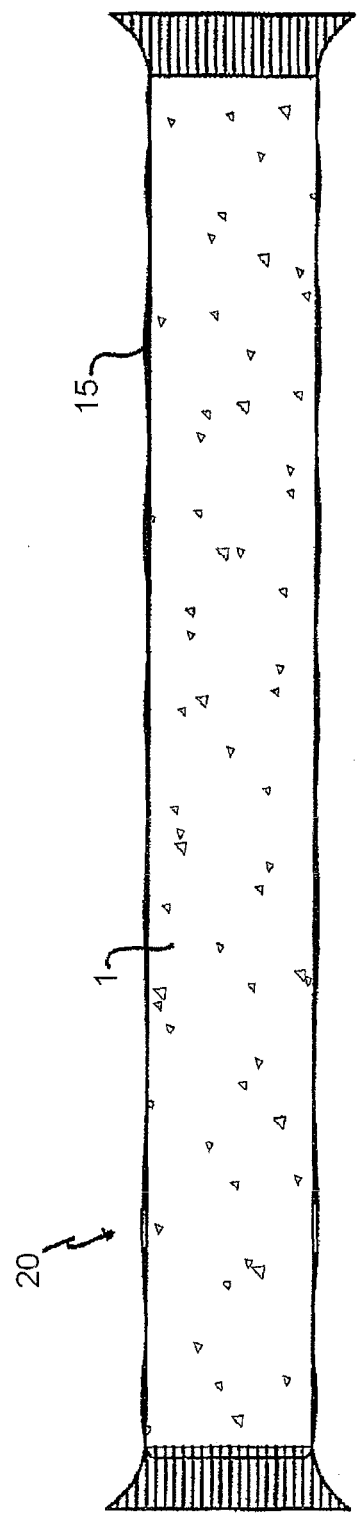
FIG. 10 is a further side view of the assembly according to the invention.

As shown in FIGS. 9 and 10, the device 1 comprises a sterile enclosure or blister 15 in order to form an assembly 20 for treatment of infections of human limbs, particularly limbs having long bones susceptible to stabilization by intramedullary nail, and to assure the highest sterility and guarantee preservation conditions before installation.

This particular configuration of the invention provides a ready-to-use device for treatment of infections, which avoids the use of skilled personnel. The device further optimizes the use of materials, by considerably reducing processing scraps.

Finally, the construction of the above assembly 20 provides a device for treatment of infections that allows reducing the time of exposure thereof to the environment and assures highly sterile conditions.

The device of this invention is susceptible of a number of modifications and changes falling within the scope disclosed in the appended claims. All the details thereof may be replaced by other technically equivalent parts, and the materials may vary depending on different needs, without departure from the scope of the invention.

Figure 12:
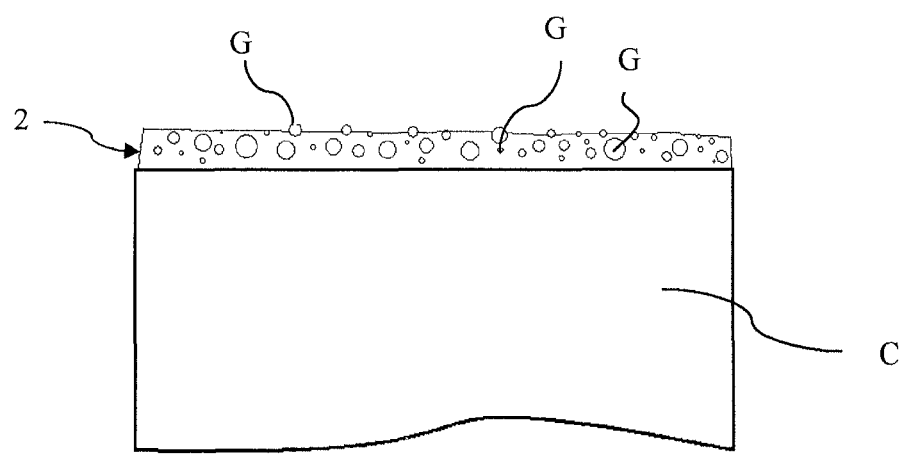
FIG. 12 is a schematic partial sectional view of a version of the device according to the invention.

FIG. 12 discloses a schematic sectional view of a version of the tubular member 2 deposited by painting over the intramedullary nail C. Inside the tubular member 2 some spherules of antibiotic G could be seen.

Figure 15:
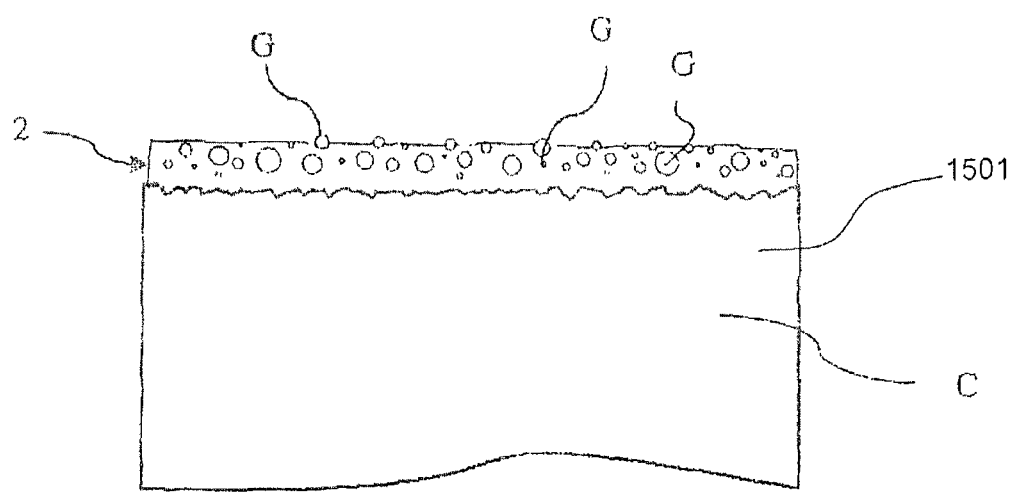
FIG. 15 is a schematic partial sectional view of another embodiment of the device according to the invention.

In a version in which the above-solution is painted onto the intramedullary nail C or onto a reinforcement core, the tubular member (of such a painted version) may be joined to the nail C and/or to a reinforcement core thanks to, e.g., an adhesive phenomenon. This adhesive phenomenon may have, e.g., mechanical and/or also chemical-physical properties. For example, the mechanical adhesion may be due to irregularity of the nail's surface (e.g., as shown in FIG. 15), such as microcavities or undercuts 1501, into which the tubular member's material 2 enters. An example of the chemical-physical adhesion may be due to the attraction induced by molecular weak forces, for example Van der Waals forces, exerted between different materials (e.g., the material of the tubular member and of the nail C).

Figure 13:
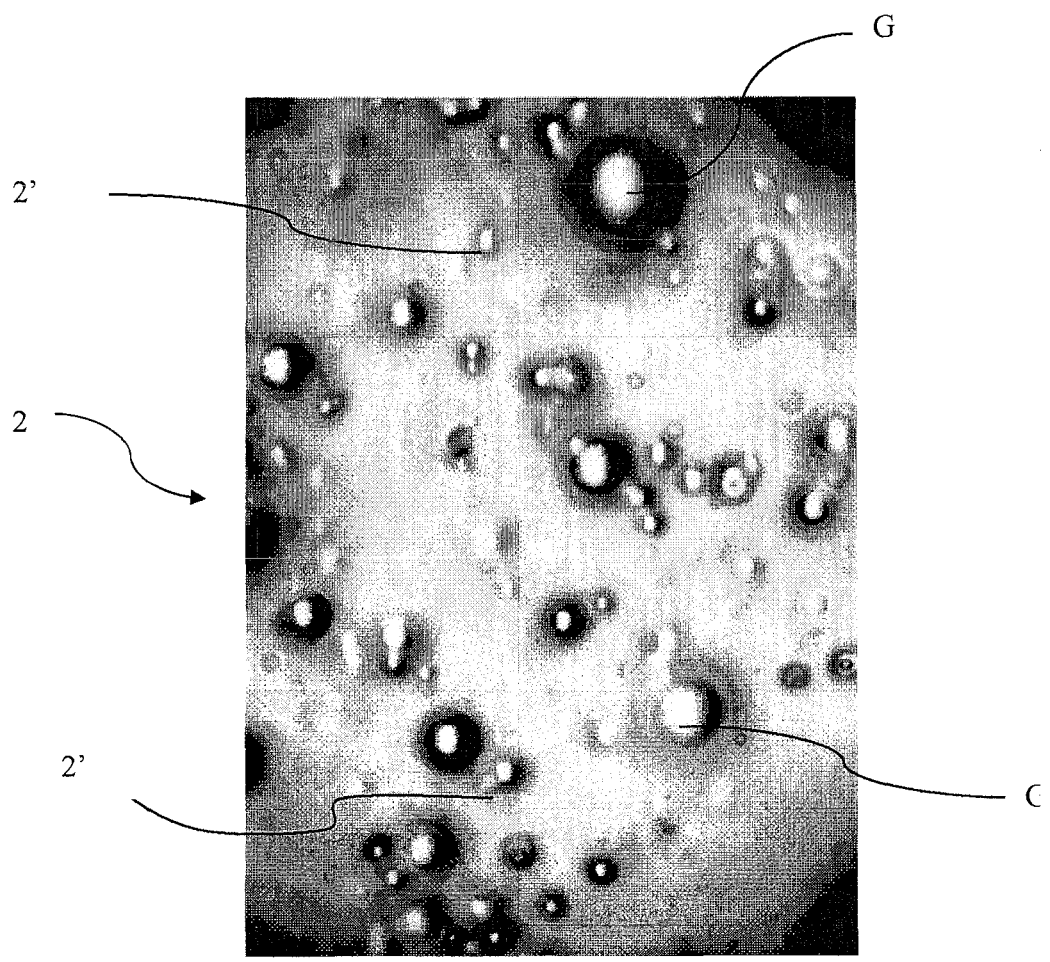
FIG. 13 is an exemplary optical microscope view of a device according to an aspect of the present invention.

FIG. 13 is an optical micrograph 2 depicting a view of a version of the tubular member 2 under magnification in which the pores 2' and the spherules of antibiotic G could be seen. This image has a 20× magnification. This image was taken about 0.1 mm below the surface of the tubular member.

Figure 14:
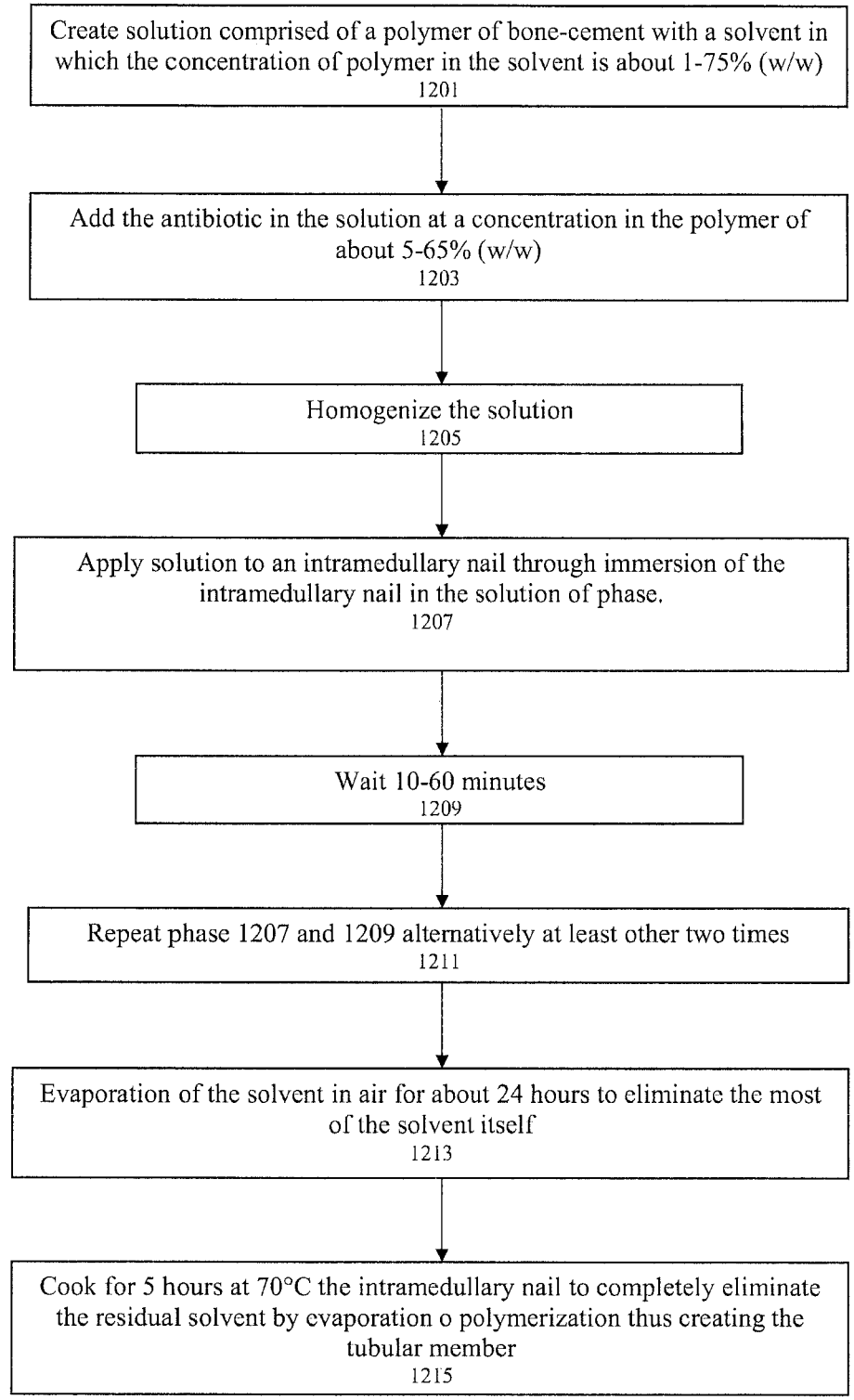
FIG. 14 is an exemplary flow chart of a method of providing a device according to an aspect of the present invention.

FIG. 14 outlines exemplary method steps of a version of the process of applying the material of the tubular member onto the intramedullary nail C. This method comprises a step 1201 of providing a solution comprised of a polymer and/or bone-cement with a solvent in which the concentration of polymer and/or bone cement in the solvent is about 1% (w/w) to about 75% (w/w), a step 1203 of adding an antibiotic in the solution at a concentration in the polymer of about 5% (w/w) to about 65% (w/w), a step 1205 of homogenizing the solution, a step 1207 of applying the solution to an intramedullary nail through immersion of the intramedullary nail in the solution of phase 1205 and emersion of the intramedullary nail, a step 1209 of waiting about 10-60 minutes, a step 1211 of repeating phase 1207 and 1209 alternatively at least other two times. The method further comprises a step 1213 of evaporation of the solvent in air for about 24 hours to eliminate the most of the solvent itself, and a step 1215 of drying for about 5 hours at about 70° C. the intramedullary nail to completely eliminate the residual solvent by evaporation and/or polymerization thus creating the tubular member and the pores 2'.

The rate of immersion of the intramedullary nail may vary between about 1 cm/min and about 60 cm/min and preferably it is about 30 cm/min; the rate of emersion may vary between about 1 cm/min and about 60 cm/min and preferably of about 5 cm/min.

Preferably the concentration of polymer and/or bone cement in the solvent is about 12% (w/w) to about 38% (w/w) and more preferably of about 25% (w/w); preferably the concentration of an antibiotic, for example gentamicin sulfate, is about 7% (w/w) to about 23% (w/w) and more preferably of about 15% (w/w). Preferably the time to step 1209 is 30 min and the number of repetition of steps 1207 and 1209 alternatively is about three more times.

In a version of the invention, at every subsequent immersion, the intramedullary nail is overturned, in order to have a uniform cover of the tubular member 2 on the intramedullary nail.

Each centimeter of intramedullary nail is covered by an amount of about 15 mg to about 60 mg of tubular member 2, and preferably by about 35 mg.

While the device has been described with particular reference to the accompanying figures, the numerals referred to in the disclosure and claims are only used for the sake of a better intelligibility of the invention and shall not be intended to limit the claimed scope in any manner.

The invention claimed is:

1. A disposable device for treatment of infections of human limbs, comprising:
   an intramedullary nail suitable for stabilization of human limbs the intramedullary nail with a distal region and a proximal region, wherein said intramedullary nail comprises two holes including a first hole located in the distal region and a second hole located in the proximal region; and
   a tubular member comprised of a relatively rigid and biologically compatible material and configured to at least partially cover said intramedullary nail, wherein said tubular member is substantially continuous and has a predetermined length corresponding to at least the distance between said first and second holes, said material comprising at least one of a porous or spongy material,
   said tubular member having a proximal region and a distal region and non-through pores integrated arbitrarily throughout the material of said tubular member,
   the tubular member including an oval-shaped hole in one of the proximal region or the distal region of said tubular member transverse to a longitudinal axis of the tubular member and for passage of corresponding screws for anchorage of the tubular member and the intramedullary nail to a bone to be stabilized, and
   said non-through pores of the material of the tubular member being impregnated with drugs or medicaments for treatment of infections, and being of a size to avoid bone growth through them.

2. The device as claimed in claim 1, wherein said material is selected from at least one of:
   the group consisting of bone cements and/or reabsorbable or biodegradable bone cements, and/or a dispersion of polymers of polymethylmethacrylate (PMMA) and/or PMMA esters, including butylmethacrylate, and/or co-polymers, including the PMMA-Polymethylstyrene, in an organic solvent or water; and/or a dispersion of polymers selected from the group consisting of polyglycolic acid (PGA), polylactic acid (PLA), L polylactic acid, L-D polylactic acid, trimethylene carbonate, polyvinylpyrrolidone (PVP) derivates, polyvinylchloride (PVC), amide or cellulose derivates and/or their isomers or racemic forms, and copolymers thereof and an organic solvent or water.

3. A device as claimed in claim 1, wherein said tubular member has a central cavity for passage of the intramedullary nail.

4. The device as claimed in claim 1, wherein said tubular member comprises a thickness of about 10-1000 micron.

5. An assembly for treatment of infections of human limbs, susceptible to stabilization by intramedullary nailing, comprising a sterile packaging blister which contains the device as claimed in claim 1.

6. The device as claimed in claim 1, wherein the pores have a dimension of about 1 to 100 micrometers.

7. The device as claimed in claim 1, wherein the pores have a dimension of about 100 microns.

* * * * *